(12) United States Patent
Gartner et al.

(10) Patent No.: US 7,709,686 B2
(45) Date of Patent: May 4, 2010

(54) PREPARATION OF GLUTARALDEHYDE

(75) Inventors: Charles D. Gartner, Midland, MI (US); Timothy D. Ligon, St. Albans, WV (US)

(73) Assignee: Dow Global Technologies Inc., Midland, MI (US)

( * ) Notice: Subject to any disclaimer, the term of this patent is extended or adjusted under 35 U.S.C. 154(b) by 0 days.

(21) Appl. No.: 12/481,181

(22) Filed: Jun. 9, 2009

(65) Prior Publication Data

US 2009/0318735 A1 Dec. 24, 2009

Related U.S. Application Data

(60) Provisional application No. 61/073,885, filed on Jun. 19, 2008.

(51) Int. Cl.
*C07C 45/42* (2006.01)
*C07C 47/12* (2006.01)
(52) U.S. Cl. .................. 568/483; 568/484; 568/485
(58) Field of Classification Search ............... 568/483, 568/484, 485
See application file for complete search history.

(56) References Cited

U.S. PATENT DOCUMENTS

| 2,546,018 | A | 3/1951 | Smith et al. |
| 3,691,205 | A | 9/1972 | Hoffmann et al. |
| 4,244,876 | A | 1/1981 | Warner et al. |
| 4,448,977 | A | 5/1984 | Warner et al. |
| 5,600,018 | A | 2/1997 | Becker et al. |
| 5,679,868 | A | 10/1997 | Kneuper et al. |
| 6,559,346 | B1 | 5/2003 | Therre et al. |

FOREIGN PATENT DOCUMENTS

| GB | 653765 | 5/1951 |
| GB | 1330055 | 9/1973 |
| JP | 7226488 | 8/1995 |
| WO | WO 99/23088 | 5/1999 |

*Primary Examiner*—Sikarl A Witherspoon

(57) ABSTRACT

Provided is a process for the preparation of glutaraldehyde. The process comprises reacting an alkoxydihydropyran with water in the presence of an acidic catalyst. The alcohol by-product distilled from the reaction mixture is subjected to a heterogeneous catalyst that is located external to the distillation column used for distilling the alcohol, thereby increasing glutaraldehyde yield and decreasing the level of alkoxydihydropyran contamination in the alcohol.

8 Claims, 3 Drawing Sheets

PREPARATION OF GLUTARALDEHYDE

CROSS-REFERENCES TO RELATED APPLICATIONS

This application claims benefit of priority from U.S. Provisional Patent Application No. 61/073,885 filed Jun. 19, 2008, which provisional application is hereby incorporated by reference in its entirety.

FIELD OF THE INVENTION

The invention relates to a process for the preparation of glutaraldehyde.

BACKGROUND OF THE INVENTION

Glutaraldehyde is prepared on an industrial scale by the hydrolysis of 2-methoxy-3,4-dihydro-2H-pyran (MDP) in the presence of an acid catalyst and water. The crude hydrolysis product is distilled to produce a methanol overheads stream, a by-product of the reaction that is itself suitable for recycling and use in other industrial processes, and a tails product containing glutaraldehyde in water. Glutaraldehyde is an important chemical that is used, for example, as a biocide or in leather tanning.

In the known processes for glutaraldehyde manufacture, some of the unreacted MDP starting material is removed, along with the methanol by-product, by the distillation process. Although the amount is generally small, the presence of the MDP in the distilled methanol is undesirable for a number of reasons, including that yield of glutaraldehyde is reduced as a result of the MDP loss, and that the MDP is a contaminant of the methanol byproduct which, as noted above, is a material that is recyclable and useful in other industrial processes.

The invention addresses the foregoing shortcomings of the current glutaraldehyde production process.

BRIEF SUMMARY OF THE INVENTION

The invention provides a process for the preparation of glutaraldehyde. The process comprises:

(a) reacting in a vessel at from 80° C. to 120° C. a reaction mixture comprising an alkoxydihydropyran compound of formula I

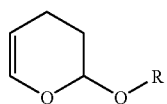

I wherein R is $C_1$-$C_{20}$ alkyl, water, and an acidic catalyst to form glutaraldehyde and the alcohol corresponding to the alkoxydihydropyran compound's alkoxy group;

(b) removing from the reaction mixture a distillate comprising the alcohol and unreacted alkoxydihydropyran compound, wherein said removal is effected with a distillation column;

(c) contacting the distillate with a heterogeneous catalyst located externally to the distillation column such that at least a portion of the alkoxydihydropyran compound reacts therein; and (d) returning at least a portion of the distillate of step (c) to the distillation column.

DETAILED DESCRIPTION OF THE INVENTION

Figure 1:
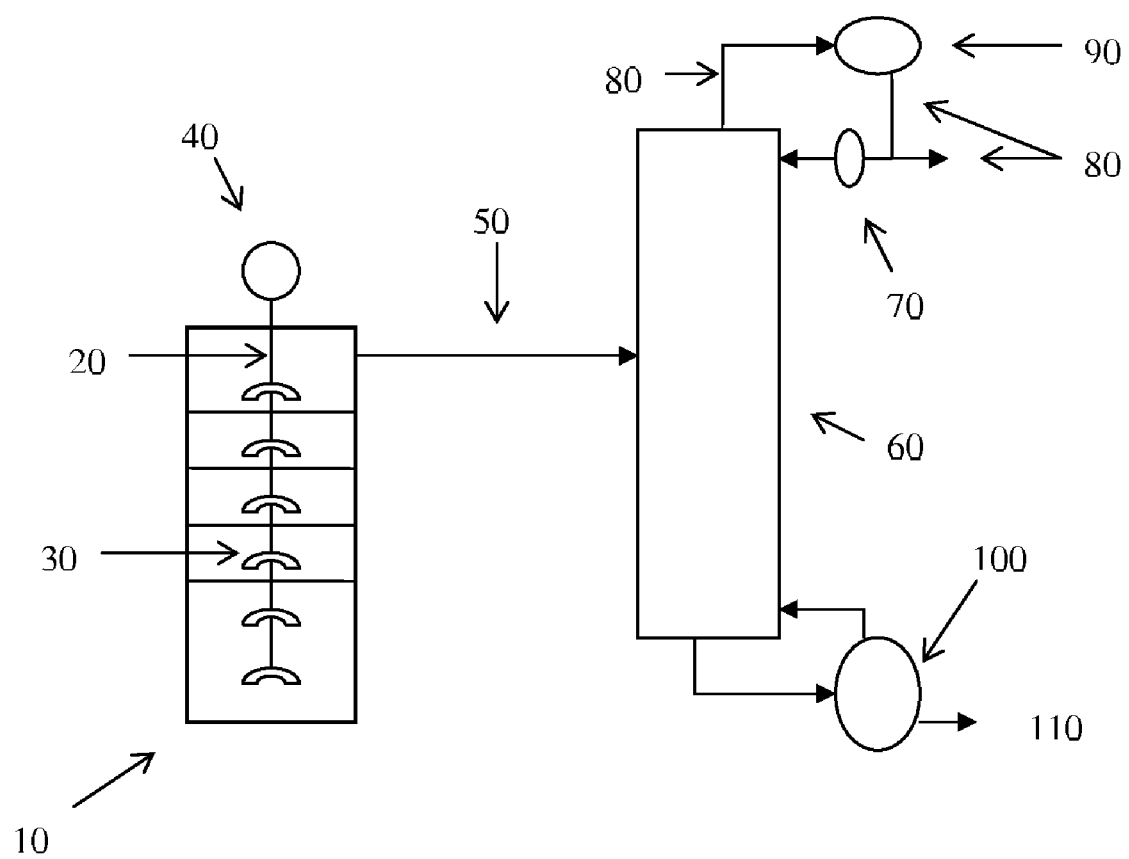
FIG. 1 is a schematic drawing of one exemplary embodiment of an apparatus that may be used to carry out the process of the invention.

As noted above, the invention provides a process for preparing glutaraldehyde. An important feature of the process of the invention is the use of a heterogeneous catalyst to effectively hydrolyze unreacted alkoxydihydropyran compound that carries over with the alcohol byproduct during distillation of the alcohol from the glutaraldehyde reaction mixture. The heterogeneous catalyst is located externally of the distillation column such that at least a portion of the column distillate can be contacted with the catalyst. By hydrolyzing alkoxydihydropyran in the distillate stream, the process advantageously increases the yield of glutaraldehyde and also provides alcohol by-product that is less contaminated with alkoxydihydropyran.

The distillation column for use in the invention is preferably a multitray setup containing sufficient theoretical plates (typically at least 2, more typically at least 20 plates) to effect the desired separation of glutaraldehyde and water from the by-product alcohol. According to the invention, the heterogeneous catalyst may be located anywhere outside the distillation column, provided that at least a portion of the distillate from the column can be contacted with it. For example, the catalyst may be located within the overheads reflux system of a typically equipped column, such as the condenser, the condenser receiver, or the line for the condensate reflux stream. As a further example, the catalyst may be located adjacent to the distillation column such that a liquid or vapor stream from any of the trays above the feed tray of the column can be passed through the heterogeneous catalyst and then returned to the column at an appropriate point. Such point is typically the same tray as the removal point, or one of the immediately adjacent trays to the removal point.

Positioning the heterogeneous catalyst according to the invention, and particularly where the catalyst is located in the overheads reflux portion of the distillation column, is advantageous since the unconverted alkoxydihydropyran is relatively concentrated at this point thereby improving its ultimate conversion into glutaraldehyde. Importantly, by positioning the heterogeneous catalyst as described herein, the advantages are achieved without significant color forming in the glutaraldehyde product. In contrast, positioning the catalyst within the distillation column, especially in the lower portions of the distillation column where significant concentrations of glutaraldehyde are present leads to polymerization of glutaraldehyde and color formation in the stream caused by the action of the catalyst on glutaraldehyde and related reaction mixture components. Positioning the catalyst in the feed line to the distillation column is also not as advantaged because of the potential for color formation in that stream.

The heterogeneous catalyst is generally an organic or inorganic acid that is affixed to a solid support. The acidic species should not significantly leach into the liquid stream flowing past it and the solid support should be stable in the presence of the attached acid and the liquid stream which it contacts. Preferred are acid functionalized resin beads (acidic ion exchange resins are one example) or zeolites or clays showing acidic functionality. Most preferred are acidic ion exchange resins, such as DOWEX MSC-1 (available from The Dow Chemical Company) and Amberlyst 15 (available from Rohm & Haas). These most preferred catalysts are particularly advantageous because they do not add substantial acidic species into the streams in contact with them.

The heterogeneous catalyst may be provided in various forms to facilitate access of the distillate to the catalyst. For instance, the catalyst may be present in a pot, a reactor, or may be in the form of a catalyst bed, filter, or slurry. Whatever the form, it should allow sufficient contact between the flowing stream and the catalyst. Preferred is a pot or reactor having a liquid distributor at the stream inlet, filled or partially filled with the heterogeneous catalyst, and then a filtering or screening device to prevent heterogeneous catalyst from flowing out of the reactor along with the stream which is returned to the distillation column.

The amount of heterogeneous catalyst desired for the invention is dependent upon several factors and can be readily determined by a person of ordinary skill in the art. The factors include: 1) the residence time (contact time) between the flowing liquid and the catalyst; 2) the temperature of the liquid and therefore the catalyst; and 3) the concentration of acidic sites on the catalyst, often expressed as milli-equivalents per cubic centimeter of resin bed volume. By way of non-limiting example, for a resin acidity of 0.1 to 2 milli-equivalents/cm$^3$ of resin bed, a typical residence time within the catalyst bed may be 10 seconds or more, and a typical temperature for the overhead reflux stream may be 40° C. to 60° C.

The process of the invention is useful for preparing glutaraldehyde from an alkoxydihydropyran compound of formula I

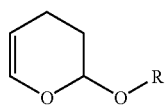

I wherein R is $C_1$-$C_{20}$ alkyl. Preferably, R is $C_1$-$C_6$ alkyl, more preferably $C_1$-$C_3$ alkyl. Most preferably, R is methyl (the compound is therefore 2-methoxy-3,4-dihydro-2H-pyran (MDP)). With MDP, the alcohol byproduct is methanol.

To prepare the glutaraldehyde, the alkoxydihydropyran of formula I is hydrolyzed with water in the presence of an acidic catalyst. In addition to forming glutaraldehyde, the reaction also forms an alcohol of formula R—OH as a byproduct. The type of vessel used for the reaction is not critical. In a preferred embodiment, the reaction vessel is equipped with a central shaft agitator powered by a drive motor and is partitioned into one or more sections which act as continuously-stirred-tank-reactors (CSTR's).

The reaction is carried out at a temperature of between 80 and 120° C., more preferably 95 to 110° C. Reaction time is typically between about 1 and 24 hours, more typically between about 1 and 3 hours.

Various acidic catalysts can be used for the bulk hydrolysis reaction, including organic acids such as saturated and unsaturated carboxylic acids having from 1 to 10 carbon atoms or polyfunctional acids such as maleic acid. Preferred are inorganic acids such as phosphoric acid, boric acid, nitric acid, sulfuric acid or acid salts, e.g. $NaH_2PO_4$. Phosphoric acid is particularly preferred. In addition to providing suitable acid strength for efficient catalysis of the reaction, phosphoric acid also generates a pH buffer once partially neutralized with a neutralizing agent, such as sodium bicarbonate. A buffered pH of about 4 stabilizes the glutaraldehyde product. The amount of acid catalyst should be such that an acid concentration in the range from 0.01% by weight to about 0.2% by weight is obtained in the reaction vessel. Typically, the acid catalyst is mixed with water at approximately 0.1% by weight and is co-fed with the alkoxydihydropyran compound into the reaction vessel. Other solvents may be used in addition or in place of the water, such as alcohol, the alkoxydihydropyran, or glutaraldehyde/water mixtures. Further additional water may be added; preferably an amount such that glutaraldehyde is obtained in the desired concentration following removal of the alcohol at the reaction's completion. Preferred glutaraldehyde concentrations are from 5 to 75% by weight, more preferably from 25 to 65% by weight.

An exemplary embodiment of the process of the invention, in operation, is illustrated in FIG. 1. Referring now to FIG. 1, an alkoxydihydropyran and water along with an acidic catalyst, the catalyst being preferably pre-mixed with the water or a portion of the water to make a solution, are fed into one end of a reactor 10 having several internal partitions making it a CSTR. Reactor 10 is further equipped with a central shaft 20, impellers 30, and drive motor 40. The reactor is preferably operated at elevated temperature, such as between 80 and 120° C., more preferably between about 95 and 110° C. Following about 1 to 2 hours of reaction time, the reactor effluent is transferred to a multi-tray distillation column 60 by pumping or pressure feed via line 50. An intermediate storage vessel can also be represented by line 50. Within the multi-tray distillation column the by-product alcohol and as noted above, minor amounts of alkoxydihydropyran (typically 2 weight percent or less), is separated from the glutaraldehyde/water product and removed from the system as distillate 80. The methanol rich distillate 80 is condensed in condenser 90 and then at least a portion of it is contacted with heterogeneous catalyst 70 which, in this exemplary embodiment, is positioned in the overheads reflux line of the distillation column. In this exemplary embodiment, a distillation reboiler for vaporizing liquid to be returned to the distillation column is shown as 100. The glutaraldehyde/water tails (bottoms) stream is shown as 110.

Contacting the portion of distillate stream 80 which is returned to the distillation column (reflux) with the heterogeneous catalyst 70 results in at least a portion of the unreacted alkoxydihydropyran in the distillate 80 to react with the by-product alcohol or water in the stream. When reacted with water, glutaraldehyde is directly produced. The glutaraldehyde thus formed increases the overall product yield. The glutaraldehyde or the alkoxydihydropyran typically also react with the alcohol in the presence of the catalyst to form other materials such as dialkoxypyrans (as well as acetals, hemiacetals, aldehydes, and the like). The dialkoxypyran materials travel down the column due to their higher boiling point and hydrolyze to form additional glutaraldehyde and alcohol below the feed tray in the column where both acid and water are present, thus further increasing glutaraldehyde yield.

The glutaraldehyde bottoms may be used without further processing, or it can be partially neutralized with a base such as sodium hydroxide, sodium bicarbonate or sodium carbonate to adjust the pH of the stream to a desired level, such as between 3 and 5, in order to increase the stability of the bottoms stream. Additional water or other formulation ingredients may be added to produce different glutaraldehyde formulated products as desired.

The following examples are illustrative of the invention but are not intended to limit its scope.

EXAMPLES

General

Figure 2:
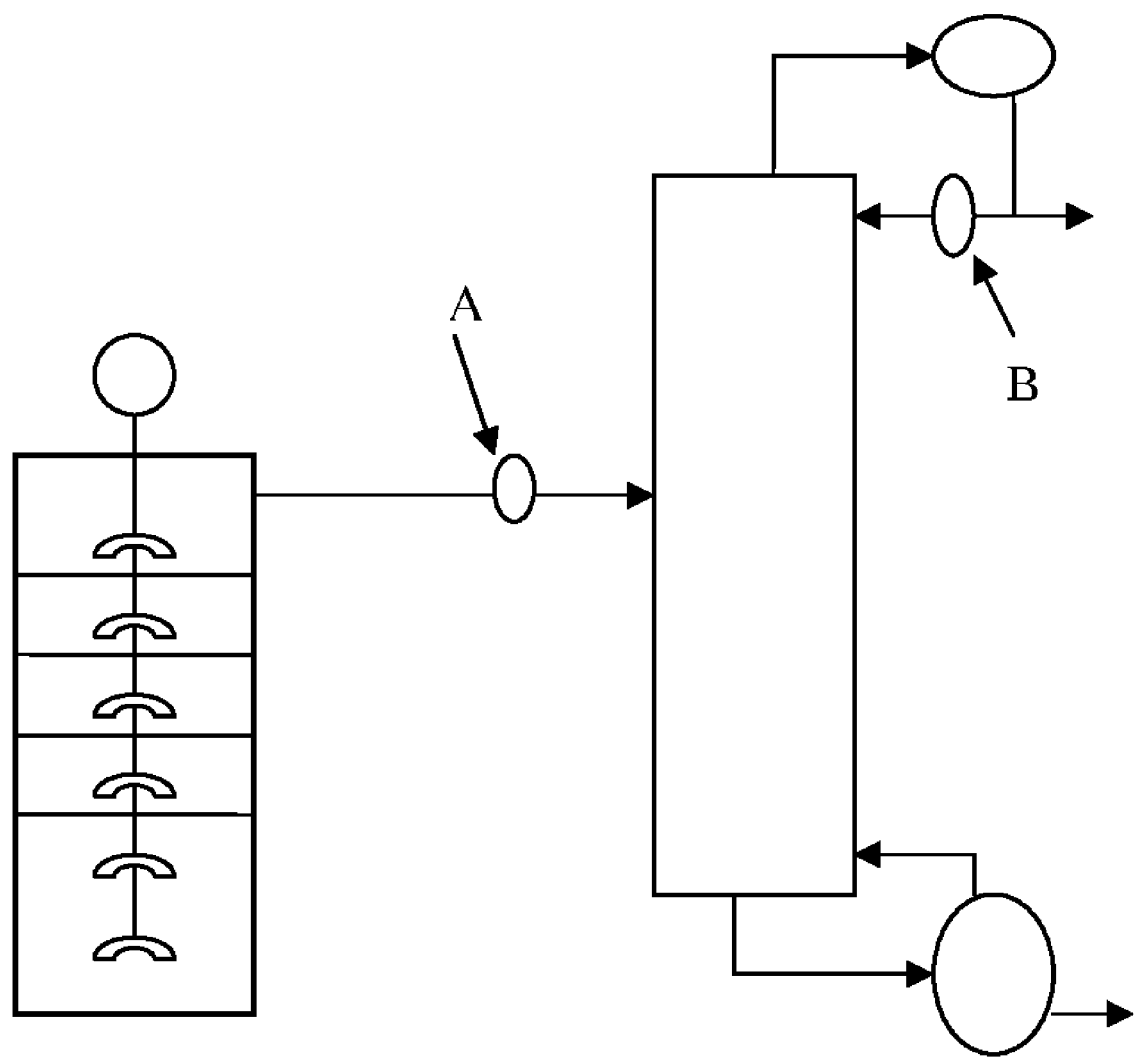
FIG. 2 is a schematic drawing of an apparatus showing placement of a heterogeneous catalyst at various locations.

The Examples compare the placement of a heterogeneous catalyst at two differing locations relative to the distillation column used for separating the alcohol from the bulk reaction. The tested locations are depicted in FIG. 2. "B" represents positioning of the heterogeneous catalyst according to the invention. "A" represents a non-invention position used for comparative purposes.

Figure 3:
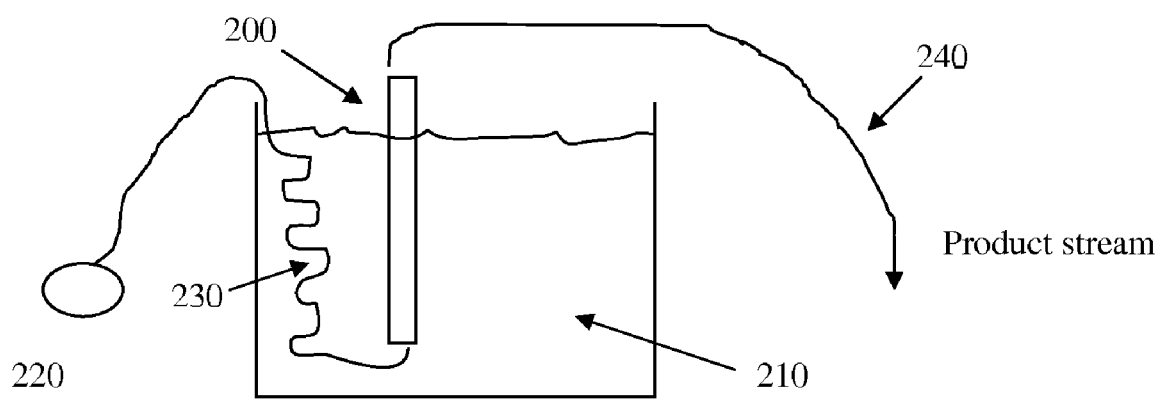
FIG. 3 is a schematic of an apparatus for testing the effect of heterogeneous catalyst location on the glutaraldehyde preparation process.

A laboratory apparatus for simulating the effect of the heterogeneous catalyst placement is used in the examples and is depicted in FIG. 3. As shown, a glass column 200 (1.5 cm inside diameter by about 25 cm long) having Teflon fittings (column to 1/8" tubing) at each end is filled with glass beads (3 mm) at either end as inert support and the central section filled with an acidic ion exchange resin catalyst. The column is immersed in a temperature controlled and stirred water bath 210. Fluid to the column is supplied by a flow calibrated peristaltic pump 220. The feed line 230 is made of 316 S.S. 1/8" tubing and coiled in the water bath to heat the feed before entering the column. Teflon 1/8" tubing 240 is used for the outlet and is used to dispense product into a sample container or a storage container as desired. The entire flow path volume from start of catalyst bed to the end of the outlet tubing is approximately 20 ml. After a feed rate change is made the system is run until at least 40 ml of feed (approximately two equipment volumes) is processed before sampling to assure that the product being sampled is representative of that flow rate. This is verified by sampling the run conditions at two different times, separated by the time it takes for at least another 20 ml of feed to be processed. If the two samples do not give similar analytical results then the times of sampling are increased until the sampling does give similar results. In these examples, MDP is used as the alkoxydihydropyran (the alcohol byproduct is methanol).

For studies at point A of FIG. 2, the purpose of the catalytic resin bed is to convert as much of the MDP to glutaraldehyde as possible. A typical composition of the feed material tested at this point is about 14 wt % MeOH, 42 wt % glutaraldehyde, 42 wt % water and 2 wt % MDP.

For studies at point B in FIG. 2, the catalytic resin bed should hydrolyze some of the MDP to glutaraldehyde and the rest of the MDP to the dialkoxylation isomers of 2,6-dimethoxy-tetrahydro-2H-pyran (both referred to here as DMTHP). A typical composition of the feed material tested at this point is about 96 wt % MeOH, 2 wt % water and 2 wt % MDP.

The first heterogeneous catalytic resin studied is Rohm & Haas Amberlyst 15-W (strongly acidic, macroreticular polymer resin beads having sulfonic acid groups used in both aqueous and non-aqueous systems. The W indicates that the resin is purchased in a water-wet state). The second resin, Dowex™ M-31, is similar to Amberlyst 15-W (strongly acidic, macroreticular polymer resin beads having sulfonic acid groups used in both aqueous and non-aqueous systems). A third resin tested is Dowex™ MAC resin (acidic, macroreticular polymeric resin beads having carboxylic acid groups used in both aqueous and non-aqueous systems). The Dowex™ MAC resin is included to determine if a "weaker" acid resin performs differently than the strong acid catalysts, especially at point A.

To simulate production plant temperatures, point A tests are run between 90 and 93° C. and point B tests are run at 41° C.

Gas Chromatography (GC) is used to examine the effluent for each experiment.

Discussion: Point A Runs

Runs at point A with strong acid catalysts (Amberlyst 15-W or Dowex M31) are found to rapidly convert the MDP but produce immediate color in the liquid. The resin also becomes dark-colored after just hours of operation. Increasing the feed rates to reduce the residence time in the catalyst bed reduces the color levels in the liquid but not as dramatically as desired. Residence times in the bed of less than 50 seconds are needed and even then the resin discolors quickly and the product gains visible color.

GC analysis shows that the MDP is greatly reduced and that several new peaks are formed. The identity of some of these peaks is determined using GC/MS to be 5,5-dimethoxy-pentan-1-al (acetal) and 1,1,5,5-tetramethoxypentane (diacetal).

Use of the Dowex™ MAC resin, having the "weaker" carboxylic acid functional groups, reduces the advent of color formation but is also less effective at catalyzing the conversion of MDP to DMTHP.

Discussion: Point B Runs

In these experiments, positioning the heterogeneous catalyst at point B is studied. A 2 wt % MDP and 2 wt % water in methanol stream is passed through a 10.6 cm$^3$ bed of Dowex™ M-31 resin at 41° C. The material, after passage through the catalyst bed, is analyzed by GC. Samples of the reaction product are taken at multiple feed rates. These feed rates correspond to volumetric space velocities (VSV's; where VSV is defined as volumetric flow rate of stream/volume of catalyst bed; i.e. gallons of feed per hour/gallons of resin bed giving units of hr$^{-1}$) ranging from 5.7 to 56.6 hr$^{-1}$. Using the area counts for the MDP peak in each of the GC traces percent conversion of MDP versus VSV can be determined. Data is provided in Table 1.

TABLE 1

| Flow Rate (ml/min) | VSV (hr$^{-1}$)[1] | MDP Area Counts | ~ % MDP reduction |
|---|---|---|---|
| 1 | 5.7 | <1,000 | 100 |
| 2 | 11.3 | <1,000 | 100 |
| 4 | 22.6 | ~1,500 | 99.5 |
| 8 | 45.2 | 10,650 | 97.0 |
| 10 | 56.6 | 23,800 | 93.3 |

[1]Volumetric space velocity, VSV, (hr$^{-1}$) = 60 * Flow rate of fluid (cm$^3$/min)/Volume of catalyst bed, where Volume of catalyst bed = Volume of resin + void volume = Total occupied space (cm$^3$).

Importantly, under all operating conditions tested with the laboratory equipment, no color was formed when the acidic catalyst was positioned at point B.

Complete conversion of the MDP to glutaraldehyde and DMTHP is not needed at point B because much of the unreacted MDP will travel through the bed again. For example at a reflux ratio of 3, 75% of this MDP will return to the reflux reactor assuming no MDP conversion occurs within the column itself. The higher the reflux ratio, the less per pass conversion of MDP is required to be readily effective.

While the invention has been described above according to its preferred embodiments, it can be modified within the spirit and scope of this disclosure. This application is therefore intended to cover any variations, uses, or adaptations of the invention using the general principles disclosed herein. Further, the application is intended to cover such departures from the present disclosure as come within the known or customary practice in the art to which this invention pertains and which fall within the limits of the following claims.

What is claimed is:

1. A process for preparing glutaraldehyde, the process comprising:
   (a) reacting in a vessel at from 80° C. to 120° C. a reaction mixture comprising an alkoxydihydropyran compound of formula I

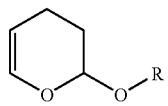

wherein R is $C_1$-$C_{20}$ alkyl, water, and an acidic catalyst to form glutaraldehyde and the alcohol corresponding to the alkoxydihydropyran compound's alkoxy group;
   (b) removing from the reaction mixture a distillate comprising the alcohol and unreacted alkoxydihydropyran compound, wherein said removal is effected with a distillation column;
   (c) contacting the distillate with a heterogeneous catalyst located externally to the distillation column such that at least a portion of the alkoxydihydropyran compound reacts therein; and
   (d) returning at least a portion of the distillate of step (c) to the distillation column.

2. A process according to claim 1 wherein the distillation column is equipped with an overheads reflux system comprising a condenser, a condenser receiver, and a condensate reflux stream line, and the heterogeneous catalyst is located in the overheads reflux system.

3. A process according to claim 2 wherein the heterogeneous catalyst is located in the condensate reflux stream line.

4. A process according to claim 2 wherein the heterogeneous catalyst is located in the condenser receiver.

5. A process according to claim 1 wherein the alkoxydihydropyran compound is 2-methoxy-3,4-dihydro-2H-pyran.

6. A process according to claim 1 wherein the heterogeneous catalyst is an acid functionalized resin bead, zeolites or clay.

7. A process according to claim 1 wherein the heterogeneous catalyst is an acidic ion exchange resin.

8. A process according to claim 1 wherein R in formula I is methyl.

* * * * *